United States Patent [19]

Smith et al.

[11] 4,038,293
[45] July 26, 1977

[54] SILICONE-COMPATIBLE TRIS(TRIMETHYLSILILYLOXY)-SILYLALKYLAMINO-SUBSTITUTED QUINONOID DYESTUFFS

[75] Inventors: Carl Mayn Smith, Sun City, Ariz.; George V. D. Tiers, St. Paul, Minn.

[73] Assignee: Minnesota Mining and Manufacturing Company, St. Paul, Minn.

[21] Appl. No.: 637,815

[22] Filed: Dec. 4, 1975

Related U.S. Application Data

[60] Continuation-in-part of Ser. No. 501,210, Aug. 28, 1974, abandoned, which is a division of Ser. No. 275,190, July 26, 1972, Pat. No. 3,888,891.

[51] Int. Cl.$^2$ .................... C07C 97/20; C07C 97/22; C07C 97/24; C07F 7/10
[52] U.S. Cl. ................. 260/378; 260/396 R; 260/448.2 N
[58] Field of Search ............. 260/378, 396 R, 448.2 N

[56] References Cited

U.S. PATENT DOCUMENTS

| | | | |
|---|---|---|---|
| 2,955,898 | 10/1960 | Bailey et al. | 260/448.2 N X |
| 2,955,899 | 10/1960 | Bailey et al. | 260/448.2 N X |
| 2,963,338 | 12/1960 | Bailey et al. | 260/448.2 N X |

*Primary Examiner*—Charles F. Warren
*Attorney, Agent, or Firm*—Cruzan Alexander; Donald M. Sell; Temple Clayton

[57] ABSTRACT

Quinonoid dyestuffs containing the tris(trimethylsilyloxy)silylalkylamino group, $-NH-(CH_2)_x-Si[OSi(CH_3)_3]_3$ are produced of the formula

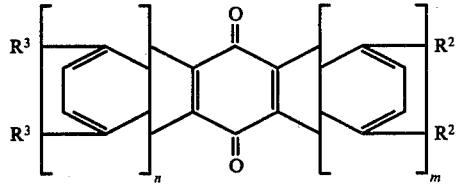

wherein each $R^2$ and $R^3$ individually is hydrogen, hydroxyl or

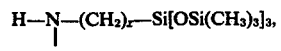

$H-N-(CH_2)_x-Si[OSi(CH_3)_3]_3$, $x$ is 1 to 6, $n$ and $m$ are independently 0 or 1 and $n \leq m$ and provided that when $n = 0$ and $m = 1$ $R^3$ is hydrogen and that when $n$ and $m$ are both 0 one each of $R^2$ and $R^3$ is hydrogen and at least one $R^3$ or $R^2$ is

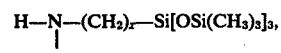

$H-N-(CH_2)_x-Si[OSi(CH_3)_3]_3$, and are found to be compatible with cured silicone polymers.

4 Claims, No Drawings

SILICONE-COMPATIBLE TRIS(TRIMETHYLSILILYLOXY)SILYLALK-YLAMINO-SUBSTITUTED QUINONOID DYESTUFFS

This application is a continuation-in-part of application Ser. No. 501,210, filed Aug. 28, 1974, now abandoned which was a division of application Ser. No. 275,190, filed July 26, 1972, now U.S. Pat. No. 3,888,891.

This invention relates to silicon-containing dyestuffs that are compatible with silicone polymers and to the process for preparing the same. More particularly, the invention is concerned with quinonoid dyestuffs containing the tris(trimethylsilyloxy)silylalkylamino group, $-NH-(CH_2)_x-Si[OSi(CH_3)_3]_3$.

Silicone polymers have been used for many years in a variety of applications because of their stability to a wide range of environmental conditions including high and low temperatures, solvents and water; and their excellent electrical characteristics. The polymers may be pigmented but have not been dyed because no readily available dyes have been found that are compatible with them. The present invention is based on the discovery of a class of hydrolytically stable, readily available dyes containing a high percentage of silicon that are compatible with silicone polymers.

A limited range of dyestuffs containing silicon are disclosed in the art. Such dyestuffs are generally prepared by the reaction of an aminoalkyl silane such as, for example, 3-aminopropyltriethoxysilane with suitable dye intermediates. Thus, Bailey and Pike in a series of U.S. Pat. Nos. 2,955,898; 2,955,899 and 2,963,338, teach the preparation of silicon-containing thiazine dyes, silicon-containing triarylmethane dyes and silicon-containing azo triazine dyes, respectively, by the reaction of a corresponding dyestuff intermediate with an aminoalkyl silane. The preparation of azo dyes containing an aminoalkyl silyl group is taught in U.S. Pat. Nos. 2,929,313; 2,927,839; 2,931,693 and 2,957,744 also issued to Bailey and Pike. These may or may not be polymerized to a polysiloxane. Hemzawi and Jones, *J. Soc. Dyers and Colourists* 85 (9), 401 (1969), describe the preparation of anthraquinone dyes containing aminoalkyl silane groups such as 3-aminopropyltriethoxysilane groups. None of the silicon-containing dyes disclosed in the foregoing references are compatible with cured silicone resins. Many are soluble in organic solvents, e.g., heptane, and low molecular weight silanes, but, when solutions of the silane containing the silicon-containing dyes are cured, syneresis forces the dye from the silicone so that completely undyed cured silicone resins are obtained.

It is an object of this invention to provide silicon-containing quinonoid dyestuffs that are compatible with cross-linked silicones.

It is another object to provide silicon-containing quinonoid dyestuffs that may be synthesized in good yields by a relatively simple process.

Other objects of the invention will in part be obvious and will in part appear hereinafter.

The dyestuffs of this invention are dyestuffs valuable in being compatible with cross-linked silicone polymers. They are structurally characterized by having, for each two aromatic rings within the dye molecule, at least one tris(trimethylsiloxy)silylalkyl group having the formula:

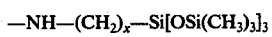

wherein $x$ is 1 to 6. The dyes of the invention are quinones of one to three aromatic rings with at least one tris(trimethylsiloxy)silylalkyl group as represented by formulae II through V in which $R^2$ is hydrogen, hydroxyl or tris(trimethylsiloxy)silylalkyl $$-NH-(CH_2)_x-Si[OSi(CH_3)_3]_3$$

wherein $x$ is as defined above.

The dyes of the invention have the formulae:

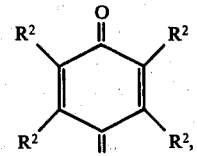

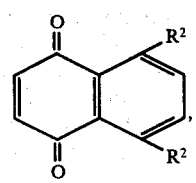

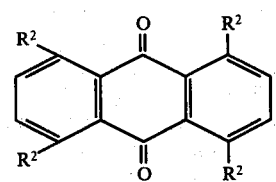

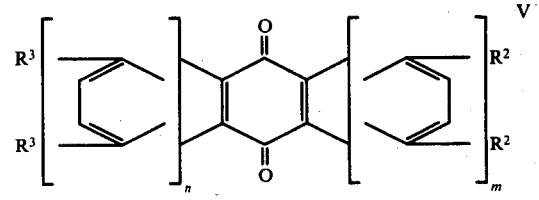

wherein each $R^2$ and $R^3$ individually is hydrogen, hydroxyl or

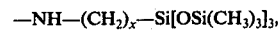

$x$ is 1 to 6, $n$ and $m$ are independently 0 or 1 and $n \leq m$ and provided that when $n=0$ and $m=1$ and $R^3$ is hydrogen and when $n$ and $m$ are both 0 one each of $R^2$ and $R^3$ is hydrogen and at least one $R^3$ or $R^2$ is

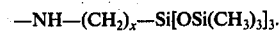

The dyestuffs of the invention are prepared by the reaction of a tris(trimethylsiloxy)silylalkyl amine having the formula:

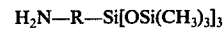

wherein R and $R^1$ are as defined above, with a susceptible chromogenic compound which is a hydroxy quinone.

Suitable tris(trimethylsiloxy)silylalkyl amines for use in the preparation of the dyestuffs of the invention include the following:
3-tris(trimethylsiloxy)silypropylamine
2-tris(trimethylsiloxy)silylethylamine 4-tris(trimethylsiloxy)silylbutylamine The tris(trimethylsilyloxy)silylalkylamines are prepared by the reaction of bis(trimethylsilyl)oxides with trialkoxysilylalkylamines in the presence of an alkaline catalyst such as, for example, quaternary ammonium hydroxides, e.g., tetraalkylammonium hydroxides, e.g., tetramethylammonium hydroxide. The reaction proceeds according to the following equation:

wherein R and R$^1$ are as hereinbefore defined and R$^3$ is lower alkyl, i.e., methyl or ethyl. The reaction takes place between about 50° and 200° C. and preferably between about 100° and 150° C. In a preferred method of preparing tris(trimethylsilyloxy)silylalkylamines, one mole of triethoxysilylalkylamine is heated with 3 moles of bis(trimethylsilyl)oxide and about 0.02 moles of tetramethyl ammonium hydroxide (20% in methanol) in an apparatus equipped for vacuum distillation through an efficient fractionating column. The pot is heated to and maintained at about 135° to 140° whereupon methanol and trimethylethoxysilane distills over at between 64° and 99° C. The tris(trimethylsilyloxy)silylalkylamine is isolated from the pot residue generally by vacuum distillation.

Quinone compounds suitable for use in the preparation of dyestuffs of the invention include benzoquinones having at least one unsubstituted alpha position, naphthoquinones and anthraquinones having at least one alpha position substituted by hydroxyl. Such quinone compounds are well known in the art and are available commercially. Typical of the suitable quinone compounds are:

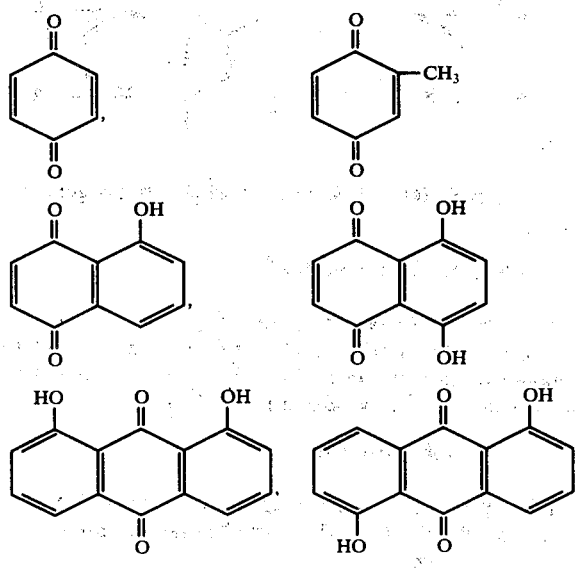

-continued

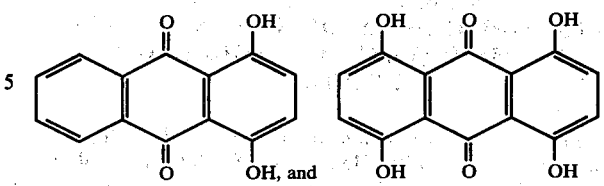

Dyestuffs of the invention are prepared from appropriate quinone derivatives by reaction thereof with 1 to 4 molar equivalents of the tris(trimethylsilyloxy)silylalkylamine using reactions which are conventional for other less complex amines. Thus, benzoquinone is reacted with 1 to 2 molar equivalents of tris(trimethylsilyloxy)silylalkylamine in a manner similar to that disclosed for the reaction of benzoquinone with amines (see, for example, Karrer, Organic Chemistry, p. 577, Elsevier Publishing Co., Inc., 1950). The hydroxynaphthoquinones and hydroxyanthraquinones are reacted with 1 to 4 molar equivalents of tris(trimethylsilyloxy)silylalkylamine in the presence of a catalyst such as boric acid or, preferably, in the presence of a reducing agent (whereon the leuco form of the quinone is formed) such as, for example, stannous chloride, stannous acetate, zinc, etc. as is disclosed in Houben, Das Anthracen and die Anthrachinone, p. 427-8, George Thieme Verlag (1929). The reaction is carried out at from 15° to 100° C. in a solvent such as, for example, ethanol and tetrahydrofuran.

Naphthoquinones and anthraquinones having negative groups other than hydroxyl, i.e., halogen, nitro, and sulfo in the alpha positions of the quinone molecule also may be used in the preparation of cross-linked silicone polymer-compatible dyestuffs of the invention. The negative group substituents on these quinones are replaced by reaction with the tris(trimethylsilyloxy)silylalkylamine in a manner analogous to that taught by Houben, loc. cit., p. 422-427 for the replacement of negative groups on anthraquinones by amino groups. This process of preparing the dyestuffs of the invention is not preferred because the use of acid receptors and higher temperatures, i.e., 100° to 200° C., are required to accomplish the reaction. These conditions tend to favor degradation and subsequent polymerization of the tris(trimethylsilyloxy)silyl groups.

Dyestuffs of the invention provide a range of colors useful for incorporation into silicone polymers and which are compatible therewith, that is, the dyestuffs are not expelled from the polymer when it is cross-linked. Illustrative examples of the dyestuffs of the invention and their colors include:

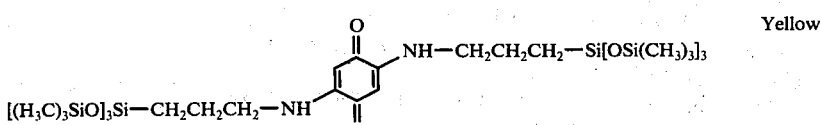

Yellow

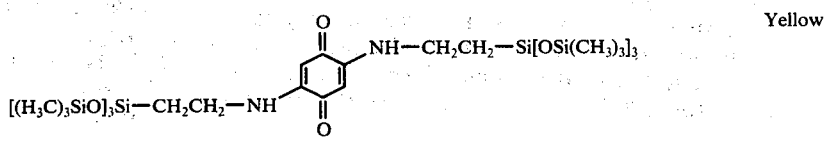

Yellow

-continued

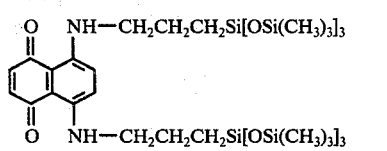    Cyan

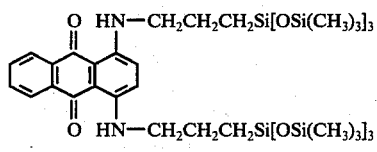    Blue

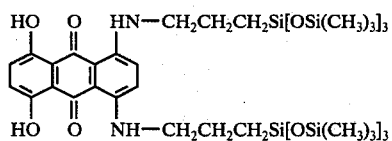    Cyan

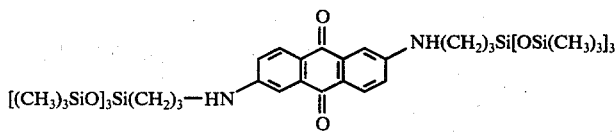    Violet

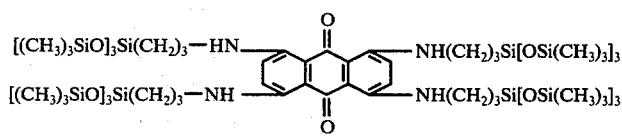    Blue

Useful silicone polymers which may be crosslinked generally and remain compatible with the dyestuffs of the invention may be selected from a broad family of silicone products including silicone polymers crosslinkable by heating with organic peroxides, e.g., silicone polymers having 0.02 to 0.5 mole-percent of methylvinylsiloxane units; and α, ω-difunctional silicone polymers which may be crosslinked by using polyfunctional crosslinking agents, e.g., hydroxyterminated polysiloxanes, commonly called "silanol-stopped fluids", crosslinked with polyfunctional crosslinking agents, e.g., methyltrichlorosilane or with certain catalysts with esters of orthosilicic, esters of polysilicic acid, alkyltrialkoxysilanes, and silanes with Si—H bonds. Other suitable difunctional silicone polymers are the diacetoxy-terminated polydimethylsiloxanes and —Si—O—N—C terminated polydimethylsiloxanes such as acetone oxime-terminated polydimethylsiloxanes having the terminal group

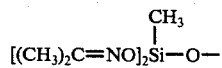

which are crosslinkable by moisture.

The dyestuffs of the invention are useful to impart color to silicone polymers that are molded and cured to resins, for example, as moldings and gaskets. The moldings and gaskets maintain the imparted color and do not expel the dyestuff. The color may be for decorative purposes or for coding purposes. Concentrations of the dyestuff in the silicone polymer may range from about 0.01% to about 5% and preferably from about 0.5 to 2% by weight whereon; in the absence of fillers, clear transparent colored polymers are obtained. A particularly useful application of the dyestuffs of the invention is to impart color to silicone polymers that are used to provide release layers such as are used in pressure sensitive tapes. Release liner papers, films or other surfaces may be coated with a solution containing about 3 to 10% curable silicone polymer and about 0.5 to about 2% of a silicone polymer-compatible dyestuff of the invention, the coating dried, and allowed to cure. The presence or lack of uniformity in the coating thickness is readily detected by observing either by eye or by instrument any variations in color density.

The silicone polymers into which the silicone polymer-compatible dyestuffs of the invention may be incorporated may also contain fillers and pigments including calcium carbonate, titanium dioxide, zinc oxide, clay, quartz flour, glass fibers, metal fibers, and the like.

The following examples are illustrative of the invention and the preparation of cross-linked silicone-compatible tris(trimethylsilyloxy)silylalkylamino dyestuffs, but are not intended in any way to limit the scope thereof.

EXAMPLE 1

Tris(trimethylsiloxy)silylpropylamine is prepared by charging a Todd still with 17.7 parts of 3-trimethoxysilylpropylamine (available from Union Carbide Corporation under the trade code Name "A1100"), 88.8 parts bis(trimethylsilyl)oxide (available from Dow Corning Corporation under the name hexamethyldisiloxane), and 1 part of a 20% solution of tetramethylammonium hydroxide. The still pot is heated to 137° C. and set to maintain this temperature. At a reflux ratio of 50 to 1, 22.7 parts of distillate is removed in about 16 hours, the head temperature rising from 64° to 99° C. There is then added 1 part of Cab-O-Sil to the still pot (to neutralize the tetramethylammonium hydroxide) and the distillation continued at about 1 mm. pressure and a reflux ratio of 5 to 1, collecting the fraction boiling 72° to 76° C. Water in an amount equivalent to the methoxy groups present in the distillate (as determined by chromatographic absorption) (approximately 1.5 parts) is added to the distillate and the mixture refluxed for 12 hours. The refluxed material is then subjected to fractional distillation and the portion boiling 74° to 78° C. at 0.95 mm. collected. There is obtained 11.2 parts of tris(-trimethylsilyloxy)silypropylamine having a purity of 96% by chromatographic absorption, a density of 0.891 g./ml. at 25° C., and a refractive index at 25% C. of 1.4117.

EXAMPLE 2

This and the following examples illustrate the preparation of tris(trimethylsilyloxy)silylalkylaminoquinones.

A flask equipped with a reflux condenser is charged with:
1.92 parts quinizarin (1,4-dihydroxyanthraquinone),
0.24 parts zinc dust,
7.00 parts 3-tris(trimethylsilyloxy)silylpropylamine, and
40 parts n-butanol The mixture is heated at reflux for 6½ hours, cooled, taken up in several volumes of heptane, filtered to remove inorganics, and the volatiles removed by heating on a steam bath. There is obtained 3.5 parts of a deep purple-blue gum which is chromatographed on SiO₂ using ethylacetate as the developer to yield 2 major components shown by infrared analysis to be

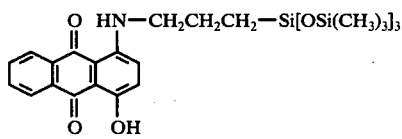

and

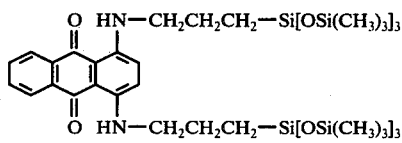

The gum itself is soluble in common organic solvents including benzene, toluene, ethylacetate, tetrahydrofuran, and silicone oils and greases. Samples of cross-linked silicone polymer placed in solutions of either dye are deeply colored blue by dye which diffuses into the polymer.

Similar results are obtained by substituting chrysazin (1,8-dihydroxyanthraquinone) or anthrarufin (1,5-dihydroxyanthraquinone) for the quinizarin in the above procedure.

EXAMPLE 3

A flask equipped with a reflux condenser is charged with:
4.12 parts leucoquinizarin (2,3-dihydro-1,4-dihydroxyanthraquinone)
15.0 parts 3-tris(trimethylsiloxy)silypropylamine, and
35 parts tetrahydrofuran,
and the mixture refluxed for 3½ hours. Volatiles are removed by heating the mixture under vacuum on a water bath to yield a residue of 15.6 parts of crude leuco dye that is taken up in 80 parts of nitrobenzene, 0.2 parts of piperidine is added and the mixture is heated 15 minutes at 100° C. to oxidize the leuco dye. Excess nitrobenzene is then stripped by heating to 130° C. under vacuum and further traces removed by taking the dye up in heptane and again stripping under vacuum. There is obtained 13.1 parts of pure blue dye containing only 1 major component. Infra red spectroscopy confirms the presence of silicone groups.

The leuco dye is also oxidized by exposing the tetrahydrofuran solution to air for about 12 hours followed by isolating the dye by stripping off the tetrahydrofuran.

The dye is soluble is common organic solvents. A solution of 1 part of dye in 100 parts of a moisture-curing single part polydimethylsiloxane is cast as a film and provides transparent deep blue cross-linked silicone polymer films. This polymer cures under the influence of atmospheric moisture without being affected by the presence of the dye which is not expelled from the film even after prolonged aging of the film.

EXAMPLE 4

The procedure of Example 3 is repeated using 3.8 parts of leuco-naphthazarin (dihyro-5,8-dihydroxynaphthoquinone-1,4) in place of the leucoquinizarin and there is obtained a cyan colored product soluble in common solvents, silicone oils and silicone greases of the structure:

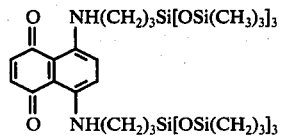

A solution of 1 part of dye in a moisture-curing single part dimethylsiloxane is cast as a film yielding a transparent deeply colored cyan cross-linked silicone film.

EXAMPLE 5

2,5-Bis[tris(trimethylsilyloxy)silylpropylaminobenzoquinone-1,4] is prepared by a reaction rather like the above.

A reaction flask equipped with a condenser is charged with:
3.24 parts benzoquinone
7.06 parts tris(trimethylsilyloxy)silypropylamine, and
40 parts ethanol.
The mixture is heated to reflux and held at reflux for about 15 minutes and then stripped of solvent by heating under reduced pressure on a steam bath. The crystalline mass is taken up in heptane, filtered to remove hydroquinone, and the heptane stripped from the filtrate by heating under reduced pressure on a stream bath. The product obtained is soluble in common solvents. When dissolved in a moisture curing single part polydimethylsiloxane and cast as a film. transparent yellow cross-linked silicone polymer films are obtained.

EXAMPLE 6

To 100 parts of a hydroxy-terminated polydimethylsiloxane, believed to have a molecular weight of about 30,000 to 50,000, (available commercially under the designation L-9000 from Union Carbide Corp.) is added 1 part of the tris(trimethylsiloxy)silylpropylamino substituted quinizarin dye prepared as described in Example 3 and 0.2 parts of stannous octoate. The mixture is stirred to dissolve the components. There is added 3 parts of tetraethyl silicate to the solution and the solution cast as a film. The film cures with the elimination of ethanol to a transparent deep blue cross-linked silicon

What is claimed is:

1. A quinonoid dyestuff of the formula:

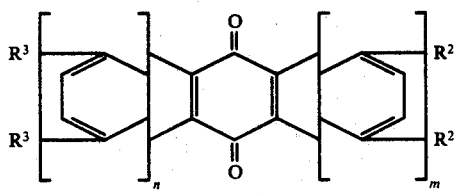

wherein each $R^2$ and $R^3$ individually is hydrogen, hydroxyl or

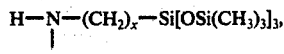

$x$ is 1 to 6, $n$ and $m$ are independently 0 or 1 and $n \leq m$ and provided that when $n = 0$ and $m = 1$ $R^3$ is hydrogen and that when $n$ and $m$ are both 0 ones each of $R^2$ and $R^3$ is hydrogen, and at least one $R^3$ or $R^2$ is

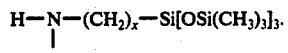

2. A quinonoid dyestuff according to claim 1 of the formula

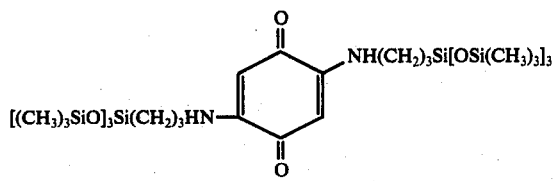

3. A quinonoid dyestuff according to claim 1 of the formula

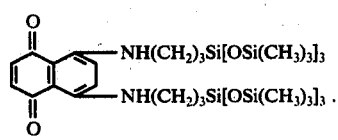

4. A quinonoid dyestuff according to claim 1 of the formula

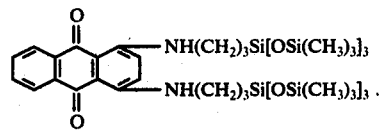

* * * * *

UNITED STATES PATENT AND TRADEMARK OFFICE
CERTIFICATE OF CORRECTION

PATENT NO. : 4,038,293
DATED : July 26, 1977
INVENTOR(S) : Carl Mayn Smith and George V. D. Tiers It is certified that error appears in the above-identified patent and that said Letters Patent are hereby corrected as shown below:

Section [54], line 2, "TRIS(TRIMETHYLSILILYLOXY)-" should read -- TRIS(TRIMETHYLSILYLOXY)- -- .

Column 1, line 3, "TRIS(TRIMETHYLSILILYLOXY)SILYL-ALK-" should read -- TRIS(TRIMETHYLSILYLOXY)SILYLALK- -- .

Column 1, line 9, -- , -- should be inserted between "doned" and "which."

Column 2, line 49, "and" between "1" and "$R^3$" should be deleted.

Column 2, line 67, "...silypropylamine" should read -- ...silylpropylamine -- .

Column 4, line 16, "...silyalkylamine" should read -- ...silylalkylamine -- .

Column 4, line 22, "silyalkylamine" should read -- silylalkylamine -- .

Column 4, line 26, "and" should read -- und -- .

Column 4, line 38, "silyalkylamine" should read -- silylalkylamine -- .

Column 7, line 6, "...silypropylamine" should read -- ...silylpropylamine -- .

UNITED STATES PATENT AND TRADEMARK OFFICE
CERTIFICATE OF CORRECTION

PATENT NO. : 4,038,293

DATED : July 26, 1977

INVENTOR(S) : Carl Mayn Smith and George V. D. Tiers

It is certified that error appears in the above-identified patent and that said Letters Patent are hereby corrected as shown below:

Column 8, line 51, "stream" should read -- steam -- .

Column 9, line 24, "ones" should read -- one -- .

Signed and Sealed this

Twenty-fourth Day of October 1978

[SEAL]

Attest:

RUTH C. MASON
Attesting Officer

DONALD W. BANNER
Commissioner of Patents and Trademarks